(12) United States Patent
Hossain et al.

(10) Patent No.: US 6,371,911 B1
(45) Date of Patent: Apr. 16, 2002

(54) SURGICAL RETRACTOR

(75) Inventors: Mosaddeq Hossain, Somerville, NJ (US); Andrew E. Fleischacker, Lower Makefield; Gerard A. Powell, Havertown, both of PA (US); John A. Fanticola, Jr., Stuart, FL (US)

(73) Assignee: Pilling Weck Incorporated, Horsham, PA (US)

( * ) Notice: Subject to any disclaimer, the term of this patent is extended or adjusted under 35 U.S.C. 154(b) by 0 days.

(21) Appl. No.: 09/635,543

(22) Filed: Aug. 10, 2000

(51) Int. Cl.[7] .................................................. A61B 1/32
(52) U.S. Cl. ....................................... 600/232; 600/231
(58) Field of Search ............................... 600/231, 232, 600/233, 235, 201, 227

(56) References Cited

U.S. PATENT DOCUMENTS

| | | | |
|---|---|---|---|
| 3,227,156 A | 1/1966 | Gauthier | |
| 4,421,107 A | 12/1983 | Estes et al. | |
| 4,852,552 A | 8/1989 | Chaux | |
| 4,989,587 A | * 2/1991 | Farley | 600/232 X |
| 5,067,477 A | * 11/1991 | Santangelo | 600/227 X |
| 6,042,542 A | 3/2000 | Koros et al. | 600/231 |

* cited by examiner

*Primary Examiner*—Jeffrey A. Smith
(74) *Attorney, Agent, or Firm*—Howson & Howson

(57) ABSTRACT

In a hands-free, spreader retractor for thoracic or abdominal surgery comprising a frame with parallel, blade-supporting arms movable toward and away from each other by a rack and pinion mechanism, plural blades are supported on the arms by depending pylons which are substantially narrower than the widths of the blades measured in the direction of elongation of the arms, to permit accumulation of fat of an obese patient between adjacent pylons. The lower portions of the pylons are connected to the undersides of the arms by narrow stems which are spaced from the edges of the arms to allow auxiliary instrument supports to slide lengthwise along the arms.

12 Claims, 2 Drawing Sheets

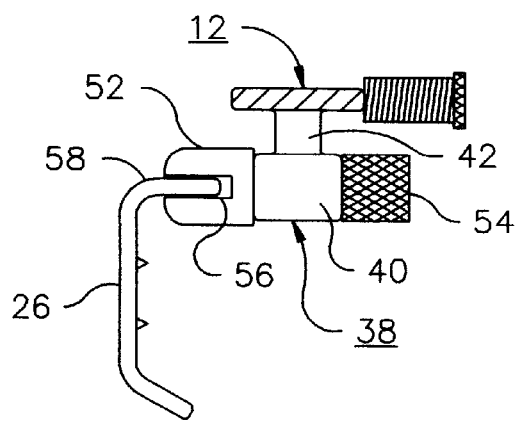
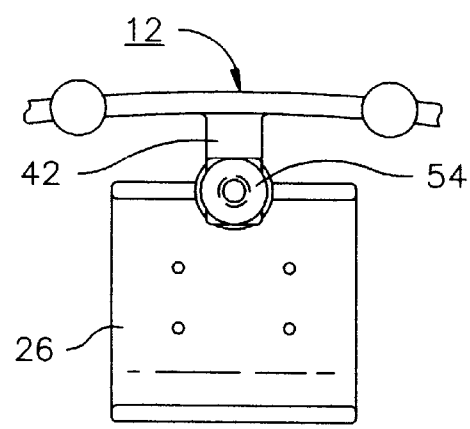
*Fig. 2*  *Fig. 3*
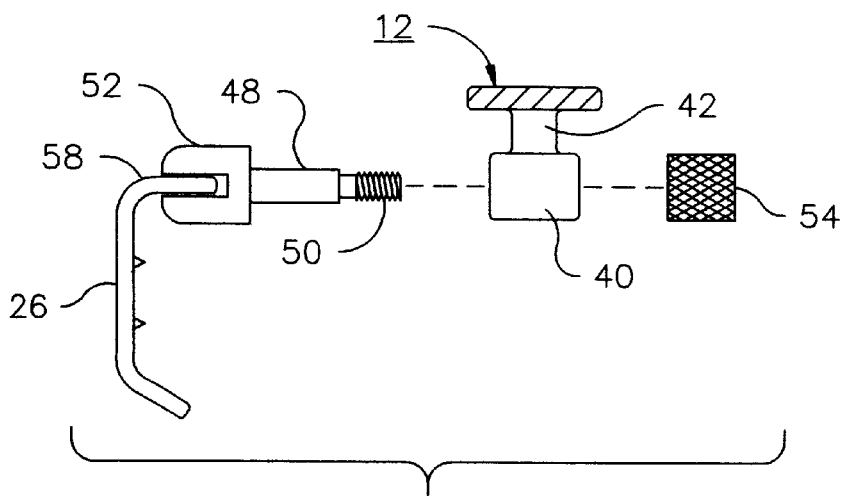
*Fig. 4*
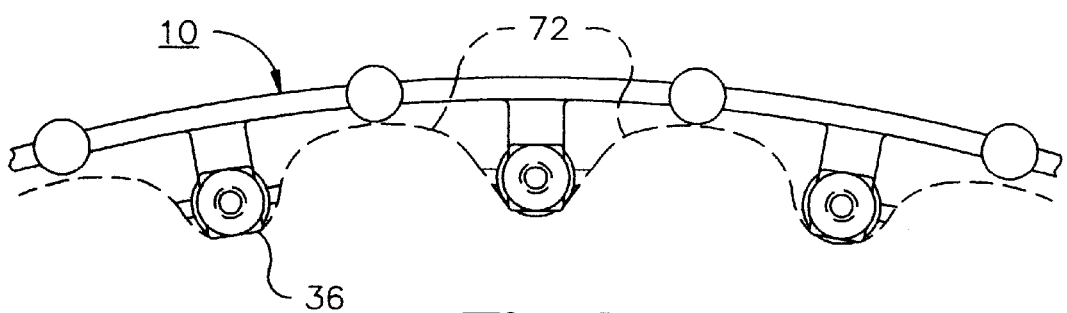
*Fig. 5*

SURGICAL RETRACTOR

FIELD OF THE INVENTION

This invention relates to surgery, and more particularly to hands-free surgical retractors of the kind in which one or more tissue-engaging elements are mounted on a frame which is supported on the patient's body.

The principal retractors of the type to which this invention relates include rib spreaders and sternal spreaders. Most of these spreading retractors have a three-sided, rectangular frame comprising a pair of arms, a first one of which is fixed in perpendicular relation to a rack, and the other of which is movable along the rack in parallel relation to the first arm by a crank-operated pinion. Other retractors to which the invention is applicable include retractors having closed frames of various shapes such as circular, oval or rectangular. Retractors in accordance with the invention are primarily used as rib or sternum retractors. However the invention has utility in various hands-free thoracic and abdominal retractors.

BACKGROUND OF THE INVENTION

A typical three-sided, hands-free, rib spreading or sternum spreading retractor has one or more blades on each of its two parallel arms for engaging the chest wall. The blades adequately grasp the opposed parts of the chest wall in most patients. However, in the case of an obese patient, the layer of fat overlying the chest wall, may hold the parallel arms of the retractor at a height so far above the chest wall that the blades cannot extend to a depth sufficient to grip the chest wall adequately. For this reason it is generally necessary to utilize a specially designed retractor with an obese patient. Alternatively, in the case of a retractor having removable blade assemblies, such as that described in U.S. Pat. No. 4,852,552, granted Aug. 1, 1989, it is possible to substitute special, extra long, blades for the standard blades.

In various kinds of surgery it is desirable to mount various auxiliary devices on the arms of a spreading retractor. In heart valve surgery, for example, it is common for a surgeon to support one or more heart valve retractors on vertical posts or T-shaped supports removably connected to a spreader arm. Similarly, in "beating heart" bypass surgery, a heart stabilizer may be secured to the spreader for the purpose of immobilizing, or at least limiting the motion of, the portion of the heart wall on which a bypass graft is to be carried out.

It is desirable to be able to position these auxiliary devices at any desired location on an arm of a spreading retractor, and to be able to move the auxiliary device easily from one location to another on the spreader arm. However, in conventional spreader retractors, the blades, or elements which connect the blades to the spreader arms, interfere with the movement of the auxiliary devices along the arms, and require the auxiliary devices to be removed and reattached to the arms if they need to be repositioned. Moreover, the blades and their connecting elements limit the positions at which auxiliary devices can be attached to the spreader arms.

SUMMARY OF THE INVENTION

The principal object of this invention is to provide an improved hands-free retractor which can be used with obese as well as with average patients. Another object of the invention is to provide a hands-free retractor on which auxiliary instrument supports can be readily mounted at any desired location and moved easily from one location to another. It is also an object of the invention to provide a hands-free retractor which combines the above advantages; i.e., one that has the ability to be used satisfactorily with an obese patient, the ability to accommodate an auxiliary instrument support at any desired position on its arms and the ability to allow sliding movement of an instrument support along the length of each arm.

A preferred surgical retractor in accordance with the invention comprises a frame adapted to rest on, and to be supported by, the anterior part of the chest or abdomen of a patient on opposite sides of an incision. The frame comprises two, elongated, rigid, blade-supporting elements disposed in opposed relationship to each other with a space between them. A plurality of separate, tissue-engaging blades is supported on each of the rigid elements. The distance between the blades on one of the rigid elements and the blades on the other of the rigid elements is made adjustable, preferably by using a rack and pinion mechanism to effect movement of the rigid elements relative to each other. Each blade is supported on its rigid, blade-supporting element by an associated pylon disposed underneath, and depending from the underside of, the blade-supporting element. Each pylon comprises a laterally extending element connected to the underside of the blade-supporting element, and the blade is connected to the pylon. The pylon is substantially narrower than the width of said blade in the direction of elongation of the blade-supporting element, and consequently the outer layers of fat of an obese patient can accumulate between adjacent pylons, allowing the blades to fully engage the edges of the chest or abdominal wall of the patient at the location of the incision.

In the preferred embodiment of the surgical retractor, each blade supporting element has parallel side edges and the pylons on each blade supporting element are connected to the underside thereof by connections spaced inwardly from the side edges. In this way, clearance is provided to allow an auxiliary instrument support with downwardly projecting side elements embracing the blade-support element, and inwardly projecting flanges engaging the underside thereof adjacent the side edges, to slide along the length of the blade supporting element past the pylons thereon.

As will be apparent, the narrow pylon configuration makes the retractor of the invention especially advantageous for use with obese patients. Moreover, the use of depending pylons with their connections spaced inwardly from the edges of the blade-supporting elements, i.e. the retractor arms, makes it possible for auxiliary instrument supports to be positioned at any desired location on the arms, and to be moved readily along the lengths of the arms.

Other objects, details and advantages of the invention will be apparent from the following detailed description when read in conjunction with the drawings.

BRIEF DESCRIPTION OF THE DRAWINGS

FIG. 2 is a cross-sectional view showing a blade and a blade-supporting pylon on the underside of a retractor arm;

FIG. 3 is a fragmentary elevational view of a retractor arm, showing the blade and pylon of FIG. 3;

FIG. 4 is an exploded view showing the parts of the assembly of FIG. 2; and

FIG. 5 is a fragmentary elevational view illustrating the surgical retractor in use.

DETAILED DESCRIPTION

Figure 1:
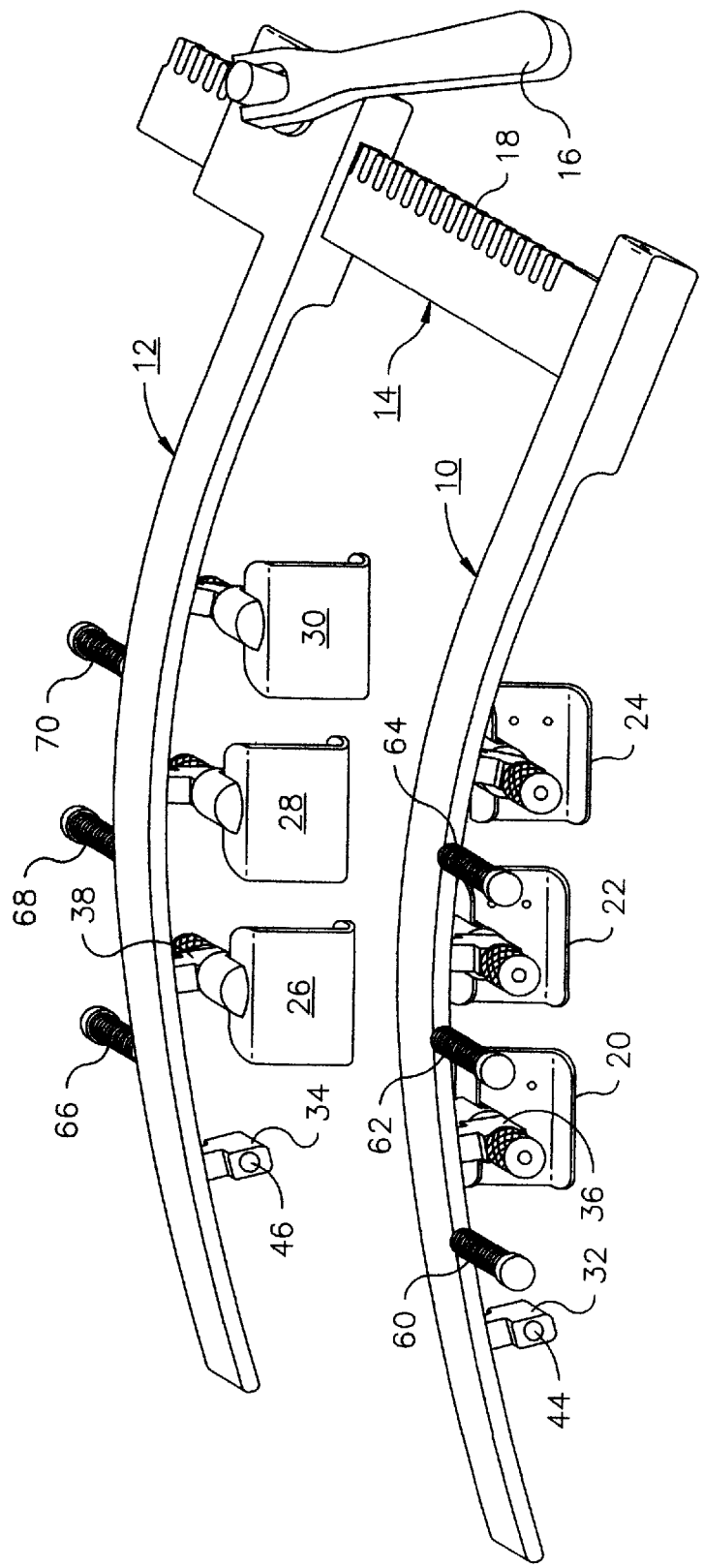
FIG. 1 is a perspective view of a surgical retractor in accordance with the invention.

The invention will now be described with reference to a sternal retractor illustrated in FIG. 1. The retractor of FIG.

1 has some features in common with conventional spreading retractors. For example, it comprises two rigid arms 10 and 12 extending in parallel relationship to each other from a rack 14. Arm 10 is fixed to the rack, while arm 12 is adapted to be moved along the rack by the operation of a crank 16 which rotates a pinion (not shown) in meshing engagement with the teeth 18 of the rack. The arms 10 and 12 are curved to accommodate the curvature of a patient's chest, and serve as supports for blades 20–30, blades 20, 22 and 24 being mounted on arm 10 and blades 26, 28 and 30 being mounted on arm 12. Each of the blades is mounted for swiveling movement relative to the arm on which it is supported about two mutually perpendicular axes. One axis is substantially perpendicular to the length of the arm and vertical when the retractor is in normal use, i.e., when the retractor arms are substantially horizontal. The other axis is substantially perpendicular to the length of the arm and horizontal when the retractor is in normal use. It will be apparent, therefore, that the blades will swivel to fit the sternum at the location of the incision, but cannot bend upward. Thus, the blades automatically achieve a firm grip on the sternum as the crank is operated to move the arms apart from each other.

In other respects the structure of the retractor in accordance with the invention departs from that of conventional spreading retractors.

Each of the blades is mounted on a retractor arm by a depending pylon. Preferably four such pylons are provided on each arm, in evenly spaced relationship to one another. The blades are removable from the pylons, and the number of blades on each arm can be varied. As shown in FIG. 1, pylon 32, one of the four pylons on arm 10, is unused. Likewise pylon 34 on arm 12 is unused. Thus, in the version of the retractor shown in FIG. 1, each arm is provided with three blades. Blade 20 is mounted on pylon 36, blade 26 is mounted on pylon 38, and the remaining blades are mounted on similar pylons.

As shown in FIGS. 2–4, pylon 38 comprises a substantially cylindrical element 40 connected to the underside of arm 12 by a stem 42. The term "substantially cylindrical" should be understood to mean only that the cross-section of the element is substantially uniform along its length. As shown in FIG. 1, the cross-section of the cylindrical elements of pylons 32 and 34 is generally rectangular, with rounded corners. The cylindrical elements of the other pylons, including element 40 of pylon 38 are similarly shaped. The cylindrical elements can, however, have various other shapes, including circular. The cylindrical element, the stem and the arm 12 are preferably welded together, although as an alternative, they can be secured together by suitable fasteners. The axis of cylindrical element 40 extends horizontally underneath arm 12 in parallel relation to the underside of the arm and laterally, preferably in perpendicular relation to the direction of elongation of the arm. The cylindrical element has a central passage extending along its axis. The central passages 44 and 46 of elements 32 and 34, respectively, are seen in FIG. 1.

As shown in FIG. 4, the central passage (not shown) of element 40, receives a pin 48, which fits snugly but rotatably in the passage. The pin has a narrow extension with threads 50 at one end and a head 52 at the other end. The pin is held in place by a nut 54 threaded onto the threads 50 of the pin extension. The unthreaded portion of the pin is circular in cross-section and smooth, and the length of the unthreaded portion is slightly greater than the length of the cylindrical pylon element, so that the pin can rotate in element 40 when the nut 54 is tightened.

Head 42 has a slot 56 (FIG. 2) receiving an upper flange 58 of blade 26. The flange is held in the slot on a captured pin (not shown) which allows the blade to rotate about an axis which is perpendicular to the axis of element 40 and parallel to the direction in which the blade 26 extends, i.e. the vertical direction in FIG. 2.

As shown in FIG. 1, each of the arms is provided with a series of suture holders, there being three suture holders, 60, 62 and 64 on arm 10 and three suture holders 66, 68 and 70 on arm 12. Each suture holder comprises a pin threaded into, and extending horizontally from, its arm, and a coil spring surrounding the pin and held thereon between a head of the pin and a suitable stop (not shown). Each pin is threaded into the outer side edge of its arm, and is removable from the arm. The suture holders, are used to secure sutures temporarily in various surgical operations, for example heart valve operations. The sutures are wound around the coil springs of the suture holders and are held between adjacent turns of the coils.

As shown in FIGS. 1 and 3, the widest parts of the pylons, are substantially narrower than the widths of the blades, as measured in directions parallel to the elongation of the arms 10 and 12. The narrow profiles of the pylons allows the pylons to penetrate the outer layers of fat on an obese patient, so that the fat layers 72 accumulate between adjacent pylons as shown in FIG. 5. The penetrating action of the pylons allows the retractor blades to achieve full engagement with the edges of the chest or abdominal wall of he patient at the location of the incision.

As best seen in FIGS. 2 and 4, the pylon stem 42 is connected to the underside of the arm 12 by connections spaced inwardly from the side edges of the arm. This provides a clearance allowing an auxiliary instrument support (not shown), with downwardly projecting side elements embracing the arm and inwardly projecting flanges engaging the underside thereof adjacent the side edges, to slide along the length of the blade supporting element past the pylons. The suture holders can easily be removed to allow sliding of the auxiliary support or to allow it to be positioned at a location at which it would otherwise interfere with a suture holder.

Although the pylon stems are narrower than the retractor arms 10 and 12, the lower elements of the pylons can be relatively long. As shown in FIG. 2, the head 52 of pin 48 projects past the inner edge of arm 12, so that blade 26 is located underneath the space between the arms 10 and 12, but close to the inner edges of the arm 12. The lengths of the lower elements of the pylons can be selected to position the blades in any desired relationship to the arms. Thus, with appropriately shaped pylons, the blades can be directly underneath the arms. Alternatively, with pylons projecting beyond the inner edges of the arms, the blades can be located well beyond the inner edges of the arms.

As will be apparent from the foregoing, the retractor in accordance with the invention has several important advantages over conventional spreading retractors, including the capability of being used satisfactorily with obese patients as well as with average patients, and an improved ability to accommodate auxiliary instrument supports.

Various modifications can be made to the retractor described. For example, although cylindrical pylons are preferable, the pylons need not be cylindrical, and can be of any desired shape so long as they are relatively narrow compared to the widths of the blades, as measured in directions parallel to the elongation of the arms. The invention is applicable to various alternative forms of retractor frames, including closed frames in which the distances between the blade-supporting elements are fixed, and the distances between opposite blades are varied by adjustment of the positions of the blades individually relative to their supporting elements.

Still other modifications may be made to the apparatus and method described above without departing from the scope of the invention as defined in the following claims.

What is claimed is:

1. A surgical retractor comprising:

a frame adapted to rest on, and to be supported by, the anterior part of the chest or abdomen of a patient on opposite sides of an incision, the frame comprising two, elongated, rigid, blade-supporting elements disposed in opposed relationship to each other with a space between them, each blade-supporting element having an upper side and an underside; and a plurality of separate tissue-engaging blades supported on each of said elongated, rigid elements, the distance between the blades on one of the rigid elements and the blades on the other of the rigid elements being adjustable; and wherein each blade is supported on its rigid, blade-supporting element by an associated pylon disposed underneath, and depending from the underside of, said blade-supporting element, each pylon comprises a laterally extending element connected to the underside of said blade-supporting element, said blade is connected to the pylon, and the pylon is substantially narrower than the width of said blade in the direction of elongation of said blade-supporting element;

whereby the outer layers of fat of an obese patient can accumulate between adjacent pylons, allowing the blades to fully engage the edges of the chest or abdominal wall of the patient at the location of the incision.

2. A surgical retractor according to claim 1, in which the laterally extending element of each pylon projects at least to a location relative to the blade-supporting element to which it is connected such that the blade connected to said laterally extending element is located underneath said space between the blade-supporting elements.

3. A surgical retractor according to claim 1, in which the laterally extending element of each pylon is substantially cylindrical in shape.

4. A surgical retractor according to claim 1, in which each blade is supported on a laterally extending element of a pylon by a pivoting connector limiting pivoting movement of the blade to pivoting movement about a first axis extending in the direction in which the laterally extending element to which the blade is connected extends and about a second axis perpendicular to said direction.

5. A surgical retractor according to claim 1, having at least three pylons on each blade-supporting element.

6. A surgical retractor according to claim 1, in which each blade is removably supported on a laterally extending element of a pylon.

7. A surgical retractor according to claim 6, in which the blade on each pylon is connected to a shaft extending lengthwise through the laterally extending element of the pylon.

8. A surgical retractor according to claim 7, in which the shaft is connected to the blade at one end of the shaft, and is threaded at its opposite end, and in which the shaft is secured to the pylon by a nut threaded onto said opposite end of the shaft.

9. A surgical retractor according to claim 7, in which the blade is connected to the shaft by a pivoting connector limiting pivoting movement of the blade to pivoting movement about a first axis extending in the direction in which the laterally extending element to which the blade is connected extends and about a second axis perpendicular to said direction.

10. A surgical retractor according to claim 1, in which the frame includes a toothed rack connected to both of said blade-supporting elements, at least one of said blade-supporting elements being movable along the rack toward and away from the other blade-supporting element and having a crank, and a pinion rotatable by the crank and engaged with teeth of the rack, the distance between the blades on one of the rigid elements and the blades on the other of the rigid elements being adjustable by operation of said crank.

11. A surgical retractor according to claim 1, in which each blade supporting element has parallel side edges and in which the pylons on each blade supporting element are connected to the underside thereof by connections spaced inwardly from the side edges thereof, whereby clearance is provided to allow an auxiliary instrument support with downwardly projecting side elements embracing the blade-support element, and inwardly projecting flanges engaging the underside thereof adjacent said side edges, to slide along the length of the blade supporting element past the pylons thereon.

12. A surgical retractor comprising:

a frame adapted to rest on, and to be supported by, the anterior part of the chest or abdomen of a patient on opposite sides of an incision, the frame comprising two, elongated, rigid, blade-supporting elements disposed in opposed relationship to each other with a space between them, each blade-supporting element having an upper side, an underside, and two side edges, the side edges being parallel to each other; and a plurality of separate tissue-engaging blades supported on each of said elongated, rigid elements, the distance between the blades on one of the rigid elements and the blades on the other of the rigid elements being adjustable;

wherein each blade is supported on its rigid, blade-supporting element by an associated pylon disposed underneath, and depending from the underside of, said blade-supporting element, the pylons on said blade supporting element being connected to the underside thereof by connections spaced inwardly from the side edges thereof, whereby clearance is provided to allow an auxiliary instrument support with downwardly projecting side elements embracing the blade-support element, and inwardly projecting flanges engaging the underside thereof adjacent said side edges, to slide along the length of the blade supporting element past the pylons thereon.

* * * * *